Figure 1:
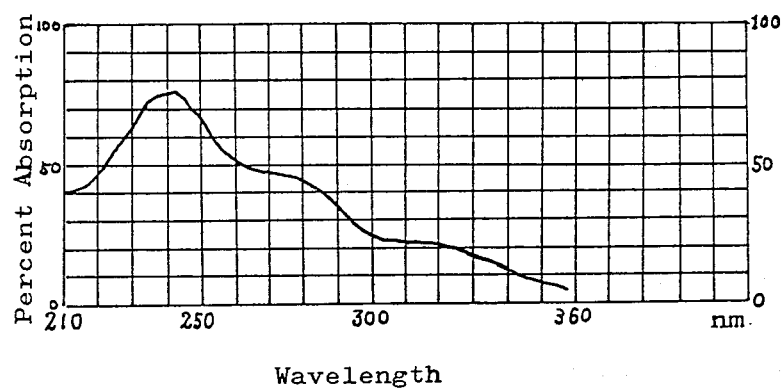

United States Patent [19]

Tanaka et al.

[11] 4,292,241

[45] Sep. 29, 1981

[54] ANTIBIOTIC PA-31088-IV AND PRODUCTION THEREOF

[75] Inventors: Kentaro Tanaka, Suita; Jun'ichi Shoji, Hirakata; Yoshimi Kawamura, Mino; Teruo Hattori, Takarazuka; Eiji Kondo, Ikeda; Kouichi Matsumoto, Toyonaka; Tadashi Yoshida, Takarazuka; Naoki Tsuji, Ashiya, all of Japan

[73] Assignee: Shionogi & Co., Ltd., Osaka, Japan

[21] Appl. No.: 115,278

[22] Filed: Jan. 25, 1980

[30] Foreign Application Priority Data

Apr. 6, 1979 [JP] Japan ................... 54-42347

[51] Int. Cl.³ .................... C07D 487/04; A61K 31/40
[52] U.S. Cl. .......................... 260/245.2 T; 424/274; 435/119
[58] Field of Search ................... 260/245.2 T

[56] References Cited

U.S. PATENT DOCUMENTS 4,172,129  10/1979  Cole et al. ............ 260/245.2 T
4,223,038   9/1980  Smale ................... 424/274

FOREIGN PATENT DOCUMENTS

| | | |
|---|---|---|
| 1628 | 5/1979 | European Pat. Off. ..... 260/245.2 T |
| 51-118701 | 10/1976 | Japan . |
| 52-1996 | 1/1977 | Japan . |
| 52-83992 | 7/1977 | Japan . |
| 52-83994 | 7/1977 | Japan . |
| 53-103401 | 9/1978 | Japan . |
| 53-109997 | 9/1978 | Japan . |
| 53-121702 | 10/1978 | Japan . |
| 54-14594 | 2/1979 | Japan . |
| 1483142 | 8/1977 | United Kingdom ......... 260/245.2 T |

OTHER PUBLICATIONS

Brown et al., J. Antibiotics 32, 961 (1979).

*Primary Examiner*—M. L. Berch
*Attorney, Agent, or Firm*—Wenderoth, Lind & Ponack

[57] ABSTRACT

A new antibiotic having β-lactamase inhibitory activity, PA-31088-IV, being useful as a medicament and a veterinary drug for inhibiting the growth of gram-positive and gram-negative phathogenic microorganisms and a process for preparing the same, being characterized by cultivating *Streptomyces tokunonensis* sp. nov. in a suitable medium and recovering PA-31088-IV from the cultured broth.

2 Claims, 2 Drawing Figures

ANTIBIOTIC PA-31088-IV AND PRODUCTION THEREOF

This invention relates to a new antibiotic, PA-31088-IV and the process for preparing the same by cultivating Streptomyces tokunonensis sp. nov. in a suitable medium and recovering PA-31088-IV from the cultured broth.

The said new antibiotic PA-31088-IV inhibits the growth of both gram-positive and gram-negative phathogenic microorganisms. Furthermore, it shows a wide range of β-lactamase inhibitory activity.

Several antibiotics are known to have a β-lactamase inhibitory activity. They are, for example, clavuranic acid (disclosed in Japanese Patent Publication (abbreviated Jap. Pat. Pub. hereinafter) (Examined No. 52-1996), MC 696-SY$_2$ (Jap. Pat. Pub. (Not-examined) No. 54-14594), MM-4550 (Jap. Pat. Pub. (Not-examined) No. 52-83994), MM-13902 (Jap. Pat. Pub. (Not-examined) No. 52-83992), MM-17880 (Jap. Pat. Pub. (Not-examined) No. 51-118701), and PS-5 (Jap. Pat. Pub. (Not-examined) No. 53-121702). Additionally, it is supposed that thienamycin, N-acetylthienamycin, epithienamycins, No. 17927A$_1$ (disclosed in Jap. Pat. Pub. (Not-examined) No. 53-103401), and 17927A$_2$ (Jap. Pat. Pub. (Not-examined) No. 53-109997) have almost the same activity. The chemical structures of some of these antibiotics are known and disclosed in J. Antibiotics Vol. 32, No. 9, 961–963 (1979).

The antibiotics PA-31088-IV is 3-[(2-acetamidoethylene)sulfonyl]-6-(2-hydroxy-1-methylethylidene)-7-oxo-1-azabicyclo[3.2.0]hept-2-ene-2-carboxylic acid of which chemical structure is shown as follows:

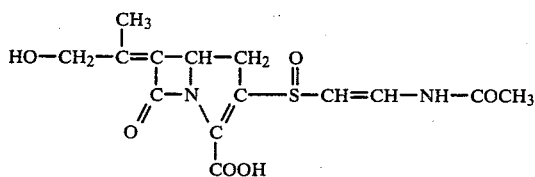

The above structure is different from those of known antibiotics having a β-lactamase inhibitory activity. Additionally, the physicochemical properties of PA-31088-IV described below proves that PA-31088-IV is different from any other known antibiotics.

The antibiotic PA-31088-IV has the following physicochemical and biological properties.

(1) Physicochemical properties of PA-31088-IV (a) Ultraviolet absorption spectrum (in 10 mM phosphate buffer): $\lambda_{max}^{H_2O}$ 241 nm (E$_{1\ cm}^{1\%}$ 562). (see FIG. 1).

Figure 2:
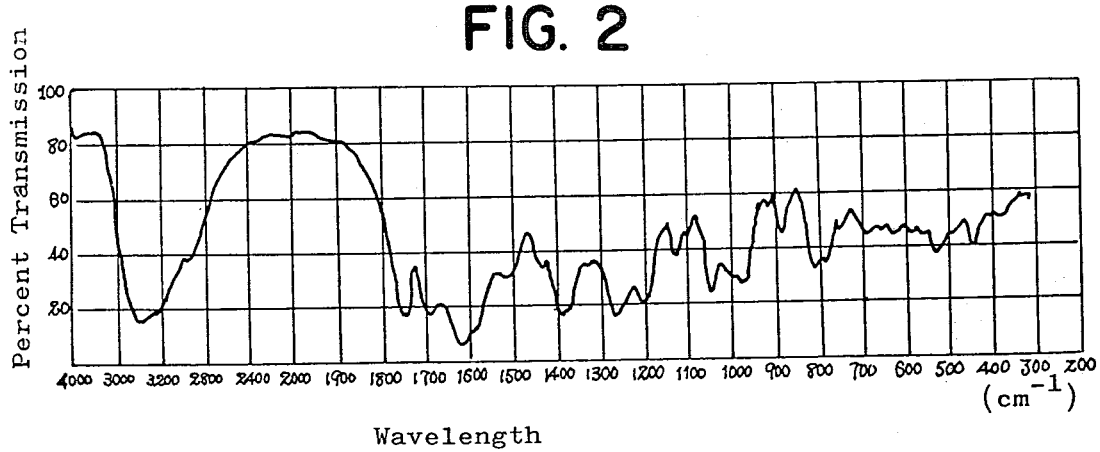

(b) Infrared absorption spectrum: $\nu_{KBr}$ 3380, 1750, 1695, 1620, 1380, 1270, 1200, 1045, 970 cm$^{-1}$. (see FIG. 2).

(c) Circular dichroism spectrum: $\lambda_{(nm)}[\theta]$ 390(0), 315(−22800), 278(−103000), 258.5(0), 243(+93300), 190(+14500).

(d) $^1$H-NMR spectrum (TMS external reference): $\delta_{ppm}^{D_2O}$ (Hz) 2.44(s,3H), 2.57(s,3H), 3.62(d-like, splitting width 9.4 Hz, 2H), 4.71(s,2H), 5.45(t-like, splitting width 9.4 Hz and 9.4 Hz, 1H), 6.79(d,1H,J=14.1), 7.98(d,1H,J=14.1).

(e) Solubility: Soluble in water, not soluble in acetone, ethyl acetate, chloroform and ether.

(f) Color reaction:
Ninhydrin reaction: negative
Ehrlich's reaction: positive (g) Acidic substance (h) Thin layer chromatography:
Rf=0.73 (70% ethanol)
Rf=0.30 (80% acetonitrile)
Rf=0.50 (chloroform/ethanol/water (4:7:2)) on cellulose plate (Eastman Co., Ltd.).

(i) $^{13}$C-NMR spectrum: $\delta_{ppm}^{D_2O}$: 15.9q, 23.0q, 32.5t, 60.4t, 64.5t, 111.7d, 134.2s, 134.7d, 135.6s, 143.2s, 150.3s, 166.7s, 173.2s, 174.6s.

(j) Mass spectrum: m/e: 355 (measured with methyl ester).

(k) Elemental analysis: Anal. calcd. for C$_{14}$H$_{15}$N$_2$O$_6$S.Na: C, 46.41; H, 4.14; N, 7.73; S, 8.84; Na, 6.35; Found: C, 45.30; H, 4.82; N, 7.74; S, 7.86; Na, 5.99.

(2) Biological properties of PA-31088-IV (a) Antibacterial spectrum

| Test Bacteria | Minimum Inhibitory Concentration (μg/ml) |
|---|---|
| Staphylococcus aureus 209P JC-1 | 3.13 |
| Streptococcus pneumoniae I | 0.39 |
| Escherichia coli NIHJ JC-2 | 3.13 |
| Klebsiella pneumoniae SRL-1 | 1.56 |
| Klebsiella sp. 363 (R) | 3.13 |
| Proteus mirabilis PR-4 | 6.25 |
| Enterobactor cloacae 233 | 3.13 |
| Serratia marcescens ATCC 13880 | 12.5 |
| Pseudomonas aeruginosa ATCC 25619 | 50 |

Note:
Inoculum size = one loopful of 10$^6$ cfu/ml (b) β-Lactamase inhibitory activity

| β-Lactamase Producing Bacteria | Minimum Inhibitory Concentration (μg/ml) |
|---|---|
| Enterobactor cloacae 92* | 0.98 |
| Klebsiella sp. 363** | 0.06 |

Notes:
*produces β-lactamase of cephalosporinase type
**produces β-lactamase of penicillinase type (c) Synergistic activity with other β-lactam antibiotics

| PA-31088-IV (μg/ml) | MIC of Ampicillin (μg/ml) | | |
|---|---|---|---|
| | S. aureus 2132 | P. vulgaris 50 | S. marcescens 39 |
| 0 | 100 | >200 | >200 |
| 2.5 | 12.5 | 6.3 | 3.1 |
| 10 | 6.3 | 1.6 | 0.1 |

| | MIC of Cefazolin (μg/ml) | | |
|---|---|---|---|
| 0 | 6.3 | >200 | >200 |
| 2.5 | 0.8 | 6.3 | 6.3 |
| 10 | 0.4 | 3.1 | 0.4 |
| MIC of PA-31088-IV | >10 | >10 | >10 |

The antibiotic PA-31088-IV is produced by a microorganism belonging to Streptomyces. The microorganism was isolated from a soil sample collected at Tokunoshima in Kagoshima Pref. Japan and tentatively named strain PA-31088. After taxonomical studies described below, the strain has been designated *Streptomyces tokunonensis* PA-31088 and deposited with the Fermentation Research Institute in Japan under accession number, FERM-P No. 4843 and with American Type Culture Collection in U.S.A. under the accession number, ATCC No. 31569.

The strain *Streptomyces tokunonensis* PA-31088 has the following characteristics:

(a) Morphological properties (cultured on Bennett's agar at 28° C. for 14 days)

Any of sporangium, flagellated spore and sclerotium are not observed. Basal hyphae are not split by fragmentation. The aerial hyphae are abundantly formed on this medium. Conidia are produced on the aerial hyphae and simply branched from main axis to form branches, of which the end is spiral. The surface of the spore is smooth and the spore is short cylindrical under electron microscopy.

(b) Cultural properties (cultured at 28° C. for 14 days)

| Medium | Growth | Aerial Hyphae Form | Color | Color of Basal Hyphae | Soluble Pigment |
|---|---|---|---|---|---|
| Sucrose Nitrate Agar Medium | Fair | Fair | Pale brown | Pale yellowish brown | None |
| Glucose Asparagine Agar Medium | " | None | — | Pale yellowish brown | " |
| Glycerine Asparagine Agar Medium | " | Little | White | Pale yellowish brown | " |
| Inorganic salt Starch Agar Medium | Good | Good | Pale reddish orange | Pale yellowish brown | " |
| Tyrosine Agar Medium | " | Fair | Pale brown | Pale yellowish brown | " |
| Nutrient Agar Medium | Fair | None | — | Pale yellowish brown | " |
| Yeast extract Malt extract Agar Medium | Good | Good | Pale reddish orange | Pale yellowish brown | " |
| Oatmeal Agar Medium | " | " | Pale reddish orange | Pale yellowish brown | " |
| Bennett's Agar Medium | " | " | Pale reddish orange | Pale yellowish brown | " |

Note:
The expression of the color is based on "The standard of the color" (Japan Color Institute).

(c) Physiological properties

Liquefaction of gelatin: poor growth
Hydrolysis of starch: positive
Tyrosinase activity: negative
Melanoid chromogenic function: negative
Peptonization of milk: positive
Coagulation of milk: negative
Utilization of carbohydrate
   Carbohydrates producing good growth: glucose, inositol
   Carbohydrates producing no growth: arabinose, xylose, fructose, sucrose, rhamnose, raffinose, mannitol
Growth temperature
   10° C.: not grow
   37° C.: fairly grow but aerial hyphae and spore are not formed.
   42° C.: not grow
   45° C.: not grow
   50° C.: not grow From the above properties, it is clear that PA-31088 strain belongs to Streptomyces.

*Streptomyces fradiae* and *Streptomyces tenebrarius* are similar to PA-31088 in that the aerial hyphae are Red color series, spore chain is spiral, the surface of the spore is smooth, and melanoid chromogenic function is negative, judged from the description in "the Actinomycetes" 2 (1961) by Wacksman, "International Journal of Systematic Bacteriology" by Shirling and Gottlieb, 18,69 and 279 (1968), 19,391 (1969) and 22,265 (1972), "Bergey's Manual of Determinative Bacteriology" the 8th edition (1974) and other published literatures of new species of actinomycetes. Especially, *Streptomyces tenebrarius* is more similar in the narrow utilization ability of sugar. However, some differences are found between the properties of PA-31088 and those of the above strains disclosed in "Antimicrobial Agent and Chemotherapy" 324 (1967). The former has no sclerotium on any medium but the latter has. The former cannot utilize fructose and sucrose but the latters can. The former peptonizes milk but not coagulates. However, the latters both peptonize and coagulate, too. The former does not grow in gelatin and is mesophilic showing no growth at a temperature higher than 42° C., but the latters are thermophilic, growing better and forming more spores at a temperature of 37° to 50° C. than at 28° C.

The former is clearly different from the latters in microbiological properties, so it is concluded that PA-31088 belongs to a new species of Streptomyces and designated *Streptomyces tokunonensis* sp. nov. The strain PA-31088 is deposited in the Fermentation Research Institute and American Type Culture Collection as noted above. This invention includes all natural or artificial mutants and variants of the above-described microorganism identified to *Streptomyces tokunonensis*. It is to be understood that this invention includes all the strains which produce PA-31088-IV and cannot be clearly distinguished from the above-described microorganism identified to *Streptomyces tokunonensis*. The artificial production of mutants may be accomplishes by a conventional operation such as X-ray or ultraviolet-ray irradiation, nitrogen mustards, 4-nitroquinoline N-oxide, N-methyl-N'-nitro-N-nitrosoguanidine and other mutagens.

The production of PA-31088-IV is carried out by cultivating the PA-31099-IV producing strain in an enriched medium under aerobic condition and PA-31088-IV is isolated from the cultured broth. A general preparation of PA-31088-IV is as follows:

The conditions of fermentation and the composition of the medium follow the usual known manner for producing antibiotics. The composition of the medium may be varied over a very wide range. It essentially consists of carbon sources, nitrogen sources and inorganic elements. Vitamins, precursors and other materials to stimulate the fermentation may be added, if necessary. Examples of the suitable carbon source are glucose, starch, dextrin, glycerol, molasses, organic acids and the like. They may be used singly or as a mixture. Examples of the nitrogen sources are soybean meal, corn steep liquor, meat extract, yeast extract, cotton seed flour, peptone, wheat germ, ammonium nitrate, which are used singly or as a mixture. The suitable inorganic elements may be chosen from, for example, calcium carbonate, sodium chloride, potassium chloride, magnesium sulfate, cobalt chloride, various phosphates, and the like. They are added to the medium if the occasion demands. Liquid media are preferred for the production on a large scale.

The fermentation may be proceeded under aerobic or submerged aerobic conditions. A submerged aerobic culture is preferable. The pH of the medium may be adjusted to about 5.5 to about 8.5. A buffering agent such as calcium carbonate may be added to the medium if the pH of the medium varies during the fermentation.

The temperature may be kept at about 20° to about 40° C., more preferably at about 25° to about 32° C., during the fermentation. The fermentation period depends on the scale. It takes for about 20 to about 80 hours on a large scale. If excessive foaming is encountered during the fermentation, antifoaming agents such as vegetable oil, lard oil, and polypropylene glycol may be added to the medium prior to or in the course of the fermentation. The antibiotic PA-31088-IV can be isolated from the fermentation broth by a per se conventional manner when the fermentation has finished. There may be employed any conventional manners such as filtration, centrifugation, adsorption and desorption with ion-exchange resins, chromatography with various active adsorbents, extract with suitable solvents and the like. The procedures may be combined properly.

In order to prevent PA-31088-IV from decomposing, a suitable stabilizing agent may be added in the step of isolation, if necessary.

As PA-31088-IV is recovered from the broth, it is preferred to use adsorption procedures when the fermentation is effected on a large scale. For example, the fermentation broth is centrifuged and the supernatant is adsorbed on a suitable adsorbent such as active carbon, diatomaceous earth, silica gel, various ion-exchange resins and porus polymers. The elution is effected with a suitable solvent such as water, saline, buffer solutions and the like. The adsorption procedure may be repeated to obtain a more purified PA-31088-IV.

Thus obtained crude PA-31088-IV may be further purified, if desired, by suitable methods such as reprecipitation, chromatography, lyophilization, and other various methods described above to be used for isolation.

Additionally, PA-31088-IV can be converted into the form of salt during the isolation procedures and also after isolation for the therapeutic and pharmaceutical use. The pharmaceutically acceptable salts are, for example, sodium, potassium, calcium and balium salts and the like.

The antibiotic PA-31088-IV is useful as a medicament, a veterinary drug, or a sterilizer for strongly acting against gram-positive and gram-negative bacteria including $\beta$-lactamase-producing strains. Therefore, PA-31088-IV and its pharmaceutically acceptable salts may be orally or parenterally administered to human or animals. The abtibiotic may be formed to tablets, capsules, powder or the like in admixture with diluents, stabilizing agents, preservatives, humidity, detergents and the like for oral administration. Further, they may be parenterally administered in the form of such as injection, ointemnt or suppository.

The dosage of PA-31088-IV is generally about 1/10 time to several times of cefalotin though it depends on the purpose of treatment. For example, the daily dosage to a human adult is about 0.1 to about 30 g in subcutaneous injection.

Having a strong $\beta$-lactamase inhibiting activity, PA-31088-IV can multiply the antibacterial activity of the $\beta$-lactam type antibiotics against $\beta$-lactamase-producing bacteria. Therefore, PA-31088-IV may be used with the well-known antibiotics of $\beta$-lactam type such as penicillins (e.g. benzylpenicillin, phenoxymethylpenicillin, carbenicillin, ampicillin, amoxicillin) and cephalosporins (e.g. cefaloridine, cefazolin, cefalexin, cefacetrile, cefamandole, cefapirin, cefradine and cefaloglycin).

The following examples are given solely for the purpose of illustration and are not to be construed as limitation of the present invention, many variations of which are possible.

EXAMPLE

(a) Fermentation Process

Medium S (preliminary seed medium): soluble starch 0.5%, glucose 0.5%, polypeptone 0.5%, meat extract 0.5%, yeast extract 0.25%, sodium chloride 0.25%, demineralized water (pH 7.0 before sterilization)

Medium B (fermentation medim): tomato paste 2.4%, dextrin 2.4%, dry yeast 1.2%, cobalt chloride.6 hydrate 0.0006%, water (pH 7.0 before sterilization)

For preliminary seed culture, *Streptomyces tokunonensis* PA-31088 (FERM-P No. 4843, ATCC No. 31569) is inoculated into a 2-liter Erlenmeyer flask containing 800 ml of Medium S of the above composition and incubated at 28° C. for 48 hours under stirring of 180 r.p.m.

The germinated seed broth (800 ml) is inoculated into a 30-liter jar containing 20 liters of Medium B of the above composition and incubated for 65 hours at 28° C. with aeration of 20 liters per minute and internal pressure of 0.5 kg/cm$^2$ under stirring of 150 to 300 r.p.m.

(b) Isolation Process

The fermentation broth is mixed with disodium ethylenediaminetetraacetate (hereinafter abbreviated as EDTA) until the concentration becomes 50 $\gamma$/ml. The supernatant fluid (100 liters) separated by means of a Sharples centrifugal separator is cooled to 10° C., adjusted to pH 7.0, passed through a column of 7 liters of Amberlite IRA-68 (Cl$^-$) (by Rohm and Haas Co., U.S.A.) at the rate of 600 ml a minute. Amberlite IRA-68 was previously equilibrated to pH 7. The column is eluted with 5% sodium chloride-cooled demineralized water. The fractions (12 liters) showing antibacterial activity checked by pulp disk diffusion method with *Escherichia coli* are collected, adjusted to pH 7.0, and passed through a column of 7 liters of Diaion HP-20 (by Mitsubishi Kasei Co.) at the rate of 120 ml a minute. The column is eluted with cooled demineralized water containing 10 $\gamma$/ml of EDTA. The active fractions (12 liters) are adjusted to pH 5.0 and 300 g of active carbon are added thereto. The mixture is stirred for 30 minutes and filtered under sucking. The carbon cake is washed with water and extracted with 50% cooled acetone containing 10 $\gamma$/ml of EDTA. The extract is concentrated under reduced pressure to a nearly aqueous solution. The residue is adjusted to pH 7.0 and lyophilized to give ca. 20 g of PA-31088-IV as a crude powder.

(c) Purification Process 1

The crude powder of PA-31088-IV (1 g) prepared as above is dissolved in 5 ml of 10 mM phosphate buffer solution (pH 7.0) containing 10 μg/ml of EDTA. The solution is applied to a column (40×350 mm) of Diaion HP-20 and developed with the above buffer solution. The fractions containing PA-31088-IV are collected and sodium chloride is added thereto until the concentration becomes 5% (weight by volume). The solution is adsorbed on a column of Diaion HP-20 and eluted with water containing 10 μg/ml of EDTA and a mixture of water-methanol (1:1). The active fractions are concentrated and lyophilized to give a brown powder (20 mg) containing 10 to 15% of PA-31088-IV. Some 240 mg of the powder can be obtained from 12 g of the starting crude powder.

Thus obtained powder is dissolved in 2 ml of 10 mM phosphate buffer solution (pH 7.0) containing 10 μg/ml of EDTA. The solution is applied to a column (25×500 mm) of Hitachi gel #3019 (by Nissei Sangyo Co.) and developed with the above buffer solution. To the active fractions is added sodium chloride until the concentration becomes 5% (weight by volume). The solution is adosrbed on the column (20×200 mm) of Diaion HP-20. The column is washed with water containing 1 μg/ml of EDTA and a mixture of water and methanol (1:1). The active eluate fractions are concentrated and lyophilized to give 50 mg of a light yellow powder containing PA-31088-IV in 50%.

(d) Purification Process 2

The powder (50 mg) obtained as above is dissolved in 10 mM phosphate buffer solution (pH 7.0) containing 10 μg/ml of EDTA. The solution is subjected to high-performance liquid chromatography on a column (10×250 mm) of Nucleocil-5$C_{18}$ (M. Nargel Co., West Germany) with a portion containing 1.5 mg of the powder at a time. The column is eluted with the above buffer solution. PA-31088-IV is detected by tracing the absorption at 240 nm with an ultraviolet absorption detector. The peak fractions containing PA-31088-IV are collected and sodium chloride is added thereto until the concentration becomes 5%. The solution is adsorbed on a column of Diaion HP-20 (20×200 mm). The column is eluted with water and a mixture of water and methanol (1:1). The active fractions are concentrated and lyophilized to give 20 mg of substantially pure sodium salt of PA-31088-IV as a pale yellowish powder.

What is claimed is:

1. An antibiotic PA-31088-IV, 3-[(2-acetamidoethylene)sulfonyl]-6-(2-hydroxy-1-methylethylidene)-7-oxo-1-azabicyclo[3.2.0]hept-2-ene-2-carboxylic acid or a pharmaceutically acceptable salt thereof.

2. The antibiotic as claimed in claim 1, of which physiochemical properties are as follows:

(a) Ultraviolet absorption spectrum (in 10 mM phosphate buffer): $\lambda_{max}^{H2O}$ 241 nm ($E_{1\ cm}^{1\%}$ 562);

(b) Infrared absorption spectrum: $\nu_{KBr}$ 3380, 1750, 1695, 1620, 1380, 1270, 1200, 1045, 970 cm$^{-1}$;

(c) Circular dichroism spectrum: $\lambda_{(nm)}[\theta]$ 390(0), 315(−22800), 278(−103000), 258.5(0), 243(+93300), 190(+14500);

(d) $^1$H-NMR spectrum (TMS external reference): $\delta_{ppm}^{D2O}$ (Hz) 2.44(s,3H), 2.57(s,3H), 3.62(d-like, splitting width 9.4 Hz, 2H), 4.71(s,2H), 5.45(t-like, splitting width 9.4 Hz and 9.4 Hz, 1H), 6.79(d,1H,J=14.1), 7.98 (d,1H,J=14.1);

(e) Solubility: Soluble in water, not soluble in acetone, ethyl acetate, chloroform and ether;

(f) Color reaction:
   Ninhydrin reaction: negative
   Ehrlich's reaction: positive (g) Acidic substance;

(h) Thin layer chromatography:
   Rf=0.73 (70% ethanol),
   Rf=0.30 (80% acetonitrile),
   Rf=0.50 (chloroform/ethanol/water (4:7:2)) on cellulose plate (Eastman Co.);

(i) $^{13}$C-NMR spectrum: $\delta_{ppm}^{D2O}$: 15.9q, 23.0q, 32.5t, 60.4t, 64.5t, 111.7d, 134.2s, 134.7d, 135.6s, 143.2s, 150.3s, 166.7s, 173.2s, 174.6s;

(j) Mass spectrum: m/e: 355 (measured with methyl ester);

(k) Elemental analysis: Anal. Calcd. for $C_{14}H_{15}N_2O_6S \cdot Na$: C, 46.41; H, 4.14; N, 7.73; S, 8.84; Na, 6.35; Found: C, 45.30; H, 4.82; N, 7.74; S, 7.86; Na, 5.99.

* * * * *